United States Patent [19]

Spitzer

[11] Patent Number: 5,031,640
[45] Date of Patent: Jul. 16, 1991

[54] PAD FOR PREVENTING CARPAL TUNNEL SYNDROME

[76] Inventor: A. Robert Spitzer, 4375 Borland, West Bloomfield, Mich. 48033

[21] Appl. No.: 440,644

[22] Filed: Nov. 22, 1989

[51] Int. Cl.$^5$ .............................................. A61F 5/04
[52] U.S. Cl. ..................................... 128/878; 128/879
[58] Field of Search ................... 273/81 R, 81 B, 81.4, 273/81.5, 81.6; 16/D12; 128/44, 77, 112, 877, 878; D8/315–318, DIG. 7

[56] References Cited

U.S. PATENT DOCUMENTS

| | | | |
|---|---|---|---|
| 31,802 | 11/1899 | Gardner | D8/DIG. 7 |
| 476,424 | 6/1892 | Smith | 16/DIG. 12 |
| 612,057 | 10/1898 | Richter | 273/81 B |
| 1,421,098 | 6/1922 | Phillips | 16/DIG. 12 |
| 2,050,176 | 8/1936 | Hammerich | 16/DIG. 12 |
| 3,327,703 | 6/1967 | Gamm | 128/77 |
| 3,344,684 | 10/1967 | Steere | 273/81 R |
| 3,713,350 | 1/1973 | Brilando | 273/81 R |
| 4,091,497 | 5/1978 | Bade | 16/DIG. 12 |
| 4,338,270 | 7/1982 | Uffindell | 16/DIG. 12 |
| 4,565,195 | 1/1986 | Eisenberg | 128/77 |
| 4,641,857 | 2/1987 | Gailiunas | 16/DIG. 12 |
| 4,785,495 | 11/1988 | Dellis | 273/81.4 |
| 4,850,341 | 7/1989 | Fabry | 128/44 |

Primary Examiner—Robert A. Hafer
Assistant Examiner—Michael Brown
Attorney, Agent, or Firm—Reising, Ethington, Barnard, Perry & Milton

[57] ABSTRACT

A cushion pad (26) for preventing carpal tunnel syndrome is adapted to be placed between the grip or shaft of a tool (14) and a hand (12). The cushion pad (26) includes a recess (28) within a predetermined size range for protecting the median nerve (24) by eliminating gripping pressure thereon. The cushion pad (26) may be configured as a cylindrical grip attached to the tool (14) or as a hand glove (40) to be placed on the hand (12) prior to grasping the tool (14). The cushion pad (26) may include positioning flanges (32, 34, 38) for positioning the median nerve (24) over the recess (28).

18 Claims, 3 Drawing Sheets

PAD FOR PREVENTING CARPAL TUNNEL SYNDROME

TECHNICAL FIELD

The invention relates to grips and pads to be used during operation of a tool for protecting the median nerve from pressure thereon preventing carpal tunnel syndrome.

BACKGROUND ART

Carpal tunnel syndrome is a common hand condition which occurs by compression of the median nerve. The transverse carpal ligament forms over the median nerve and may compress it as a result of pressure on the hand, producing symptoms of pain or numbness associated with carpal tunnel syndrome. If the median nerve is injured at the wrist, as by wounds or a dislocated lunate bone, sensation is lost in the skin on the front of the index finger and adjacent part of the thumb and over the back of the distal phalanges of the thumb, index and middle fingers, and is diminished over a large area. The brunt of the paralysis falls on the muscles of the thenar eminence which, in time, flattens as they waste. Treatment of carpal tunnel syndrome varies according to the severity of the condition. Sever conditions usually require hand surgery to sever the transverse carpal ligament, whereas less sever cases utilize a splint which immobilizes the wrist. Carpal tunnel syndrome is a particular problem for workers in industries which require manual operations with a hand held implements or tools.

U.S. Pat. No. 4,850,341, issued July 25, 1989 in the name of Fabray et al discloses a glove for preventing or inhibiting carpal tunnel syndrome. The glove includes a pad disposed over the median nerve of the hand. The pad is secured to the glove body and extends from near the wrist opening of the glove to about the center of the glove which covers the palm. The pad is made of a resilient flexible material which is effective to provide protection from vibration and shocks. The problem with such a device is that the pad is placed directly over the median nerve. With this type of pad, pressure between the median nerve and the finger-flexor tendons is increased, and, as repetitive finger movements are made, there is a potential for frictional injury.

There are many different types of hand grips available which provide a pad for comfort and to prevent vibration from causing injury to the hand. Such pads are normally made of a continuous rubber material, or may include grooves which are decorative in nature. There is no pad which eliminates continuous pressure directly over the median nerve thereby preventing carpal tunnel syndrome.

SUMMARY OF THE INVENTION AND ADVANTAGES

The invention is a hand grip assembly for placement between a tool and a hand. The assembly includes support means having first and second sides for receiving the gripping pressure of a palm of the hand on the first side and receiving a tool on the second side. The first side of the support means includes protection means recessed relative to the remainder of the first side for eliminating the gripping pressure directly over the median nerve of the hand.

The advantages of the invention include a pad which is designed to distribute pressure away from the nerve and onto adjacent soft tissue structures. The region over the nerve has no material thereover, or a material significantly softer than the surrounding pad material. This is functionally superior because pressure over the nerve is reduced, and also because the component of injury due to tendon movement is reduced.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
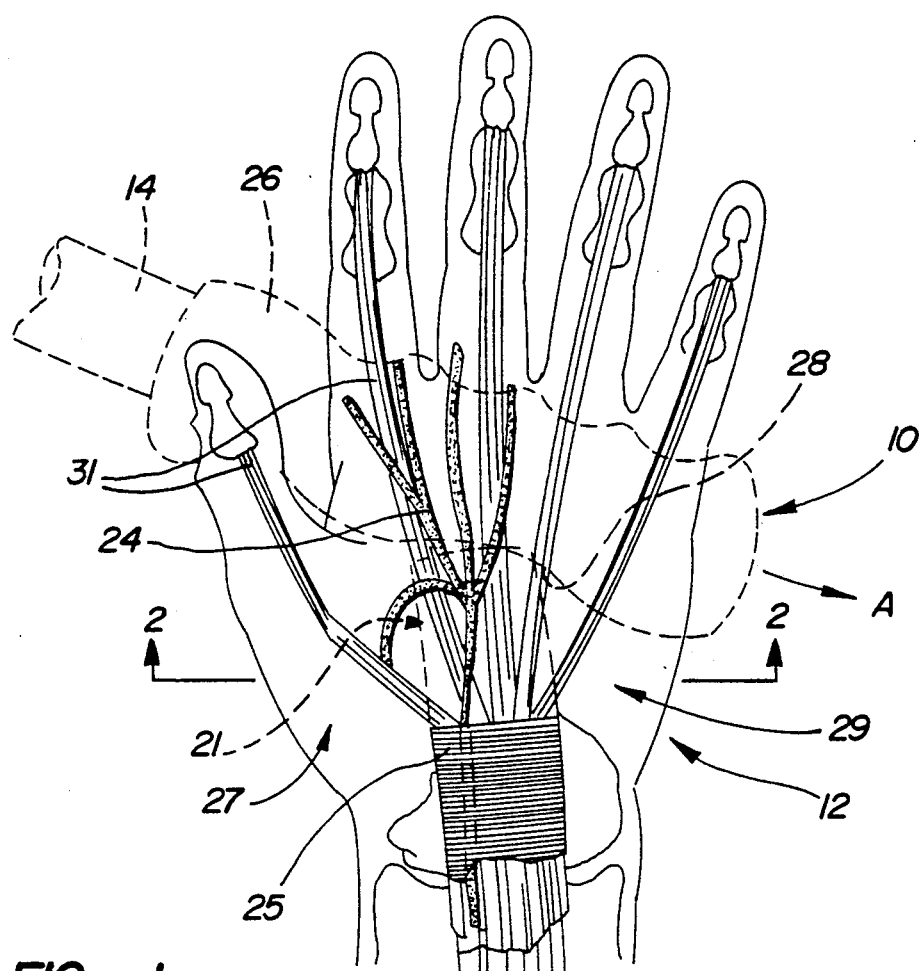
FIG. 1 is a diagram of the hand utilized with the subject invention prior to gripping same.
Figure 2:
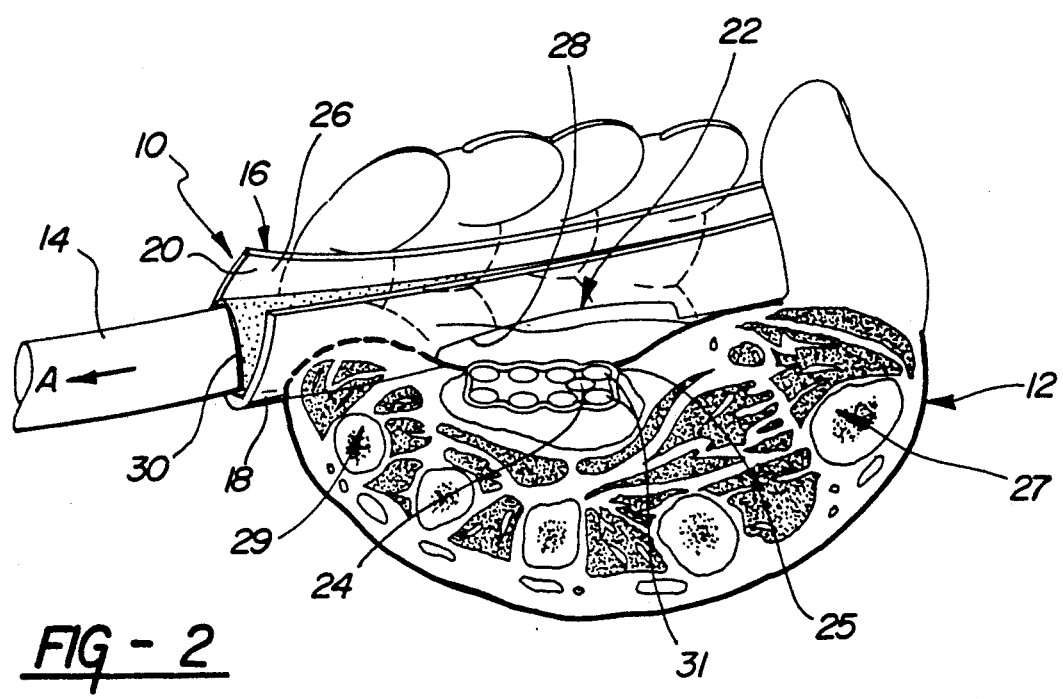
FIG. 2 is a diagram of the hand taken along lines 2—2 of FIG. 1 in a gripping position.

A hand grip assembly for placement between a tool 14 and a hand 12 to protect the hand 12 is generally illustrated in FIG. 1. The hand grip assembly 10 includes support means 16 for receiving the gripping pressure of a palm of a hand 12 on a first side 18 thereof and for receiving a tool 14 on a second side 20 thereof. The first side 18 of the support means 16 includes protection means 22 recessed relative to the remainder of the first side 18 for eliminating pressure directly over the median nerve 24 of the hand 12. The gripping pressure is defined by pressure placed on the hand 12 either by pressure as a result of weight applied by the grip of the tool 14 to the hand 12 or weight applied by the hand 12 against the grip of the tool 14, or merely by the pressure developed by grasping the grip of the tool 14.

The hand 12 and median nerve 24 are illustrated in FIG. 1. The median nerve 24 flattens out under the flexor retinaculum 25 and deep to the superficial palmar arch and the palmar aponeurosis, lying on the flexor tendons, divides into five terminal palmar digital branches 31 and a muscular branch 33. The tendous and median nerve 24 are packed within and extend through the flexor rentinaculum 25. The hand grip assembly 10 distributes pressure away from the median nerve 24 and onto adjacent soft tissue structures of muscle and fat. The areas adjacent to which pressure is distributed are the themar eminence 27 and hypothemar eminence 29. The region over the median nerve 24 has no material thereover, or may contain a material sufficiently softer than the surrounding material, as subsequently described. Therefore, pressure is eliminated from directly over the median nerve 24 and pressure is eliminated from directly surrounding the median nerve 24 to allow the tendon and therefore median nerve 24 to move without frictional injury to the median nerve 24. FIG. 1 illustrates the region over the median nerve 24 which request protection, generally indicated at 21.

The support means 16 includes a cushion pad 26 of a first predetermined resiliency and hardness. The cushion pad 26 may be made of foam, rubber, plastic, etc. The cushion pad 26 must be of a resiliency and hardness to prevent the hand 12 from resting directly on the grip of the tool 14, and particularly to prevent the median nerve 24 from receiving any significant pressure by the tool 14.

The protection means 22 comprises a recess 28 within the cushion pad 26. The recess 28 is within a predetermined size range for eliminating pressure directly over and in the vicinity of the median nerve 24. The recess 28 is placed directly over the median nerve 24 and extends to surrounding soft tissues. The median nerve 24 is approximately three millimeters wide between the base of the thumb and opposite side of the wrist, and should have protection between the crease of the wrist and the first creases of the palm. Therefore, the recess 28 must be of greater size than the median nerve 24. The recess length along the longitudinal axis A of the cushion pad 26 is approximately 2-2.5 centimeters. The recess width is perpendicular to the axis A and is at least four centimeters long. These sizes are for an average adult, therefore, the sizes may vary depending on the size of the person. The area should allow some error in positioning the median nerve 24 within the recess 28. The depth of the recess 28 and resiliency and hardness of the cushion pad 26 must be such that when pressure is placed on the hand 24 depressing the cushion pad 26, the median nerve 24 will not contact the grip of the tool 14. The median nerve 24 is supported away from the surface of the tool 14.

The recess 28 must be of a size large enough to actually relieve pressure on the median nerve 24 at the depth beneath the skin of the hand 12. The flexar retinaculum 25 is approximately two centimeters wide, therefore the recess 28 width must be larger than the flexar retinaculum 25. It should be clear that the width of the pressure release lessens further beneath the skin of the hand 12. The most sensitive to pressure area 21 of the median nerve 24 is located between the base of the thumb and the side of the wrist at the ulnar nerve. The actual position of the median nerve 24 varies from center and toward the thumb. As previously stated, the pressure sensitive area 21 of the median nerve 24 includes the width of the flexor retinaculum 25 and extends between the crease of the wrist to the first crease of the palm of the hand 12, which is approximately 4 centimeters. If the recess 28 is too small, pressure will not be inhibited on the median nerve 24, and small displacement of the hand 12 and median nerve 24 will reduce the effectiveness of the assembly 10. It is important to eliminate pressure on the protection area 21 because the median nerve 24 is just below the surface of the skin and packed in tight by the bones and flexor retinaculum 25 which is susceptible to inflammation from repeated use, and which provides no release of pressure due to the tight packing. The recess 28 allows room for the area to swell. Outside the protected area 21, the median nerve 24 is a deep within bones and muscle which is substantially unaffected by the gripping pressure. Furthermore, the median nerve 24 is loose so it may move and slide.

The cushion pad may be adapted to a variety of tools or embodiments. In four embodiments of the assembly 10a-d, the cushion pad 26a-d is utilized as a tool grip or hand grip which is initially placed about the grip or shaft of the tool 14 prior to grasping the tool 14. In a fifth embodiment of the assembly 10e, the cushion pad 26e is adapted to be inserted within a hand glove 40 and placed on the hand 12 prior to grasping the tool 14. Common reference numerals in each embodiment indicate common structure wherein each reference numeral includes a letter suffix a-e associated with the embodiment.

In the first four embodiments of the assembly 10a-d, the cushion pad 26a-d is adapted to be secured about the grip or shaft of the tool 14, and includes means 30 for securing the cushion pad 26a-d about the grip of the tool 14 to position the recess 28a-d to receive the median nerve 24 of the hand 12. The means 30 may be an adhesive to adhere the ends of the cushion pad 26a-d together forming a cylinder for receiving the grip of the tool 14, or may adhere the cushion pad 26a-d directly to the surface of the grip of the tool 14. The cushion pad 26a-d may be formed as an integral hollow cylinder to slide onto and fit about the shaft or grip of the tool 14 without use of the adhesive 30.

The cushion pad 26a-d may be adapted to a variety of tools, such as knives, clippers, crutches, bicycle grips, power tools, etc. Any tool 14 which the hand 12 must grasp and which exerts pressure on the hand 12 is considered to fall within the applications of the subject invention.

Figure 3:
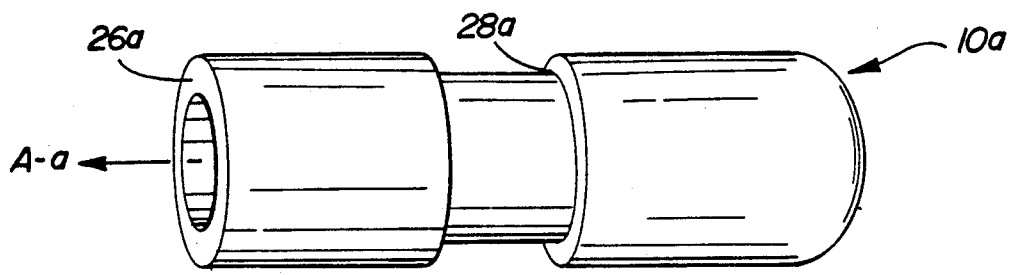
FIG. 3 is a perspective view of a first embodiment of the subject invention.

As illustrated in FIGS. 3-6, the cushion pad 26a-d may be configured in a variety of embodiments, four of which are illustrated. As illustrated in FIG. 3, the first embodiment of the assembly 10a utilizes the hollow cylinder of the cushion pad 26a which includes the recess 28a comprising an inset groove which extends about the circumference of the cushion pad 26a. When the hand 12 grasps the grip of the tool 14 about which is placed the cushion pad 26a, the median nerve 24 is located over the recess 28a preventing direct pressure thereon and allowing movement thereof. This embodiment of the assembly 10a is advantageous due to the continuous groove 28a. The hand may be placed at any circumferential position as long as the hand 12 is properly longitudinally placed on the cushion pad 26a along axis A-a.

Figure 4:
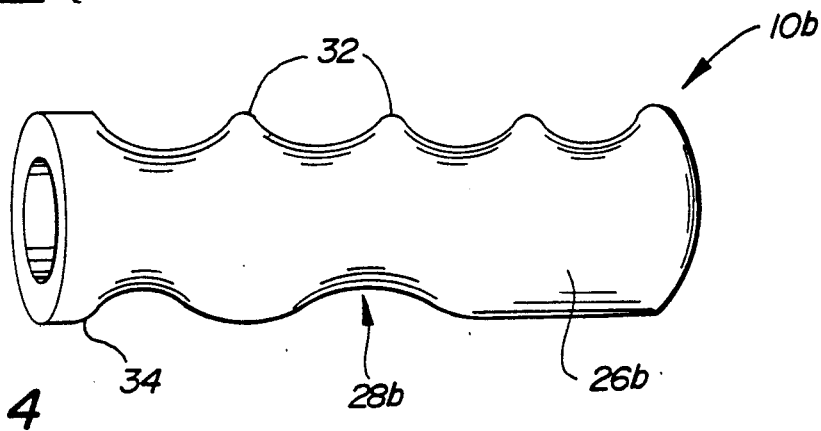
FIG. 4 is a perspective view of a second embodiment of the subject invention.

FIG. 4 illustrates the second embodiment of the assembly 10b wherein the cushion pad 26b includes a plurality of finger flanges 32 and a thumb flange 34 for receiving and positioning the fingers and palm of the hand 12 on the cushion pad 26b to position the median nerve 24 over the recess 28b. The finger 32 and thumb 34 flanges accurately position the median nerve 24 over the recess 28b to prevent pressure on or near the median nerve 24. The recess 28b is not continuous around the circumference of the cushion pad 26b as in the first embodiment 10a, the recess 28b is of the minimum size as discussed hereinabove. The finger flanges 32 and thumb flange 34 ensure proper positioning of the median nerve 24 therefore the recess 28b is of minimum size. This provides additional support for the fingers of the hand 12.

Figure 5:
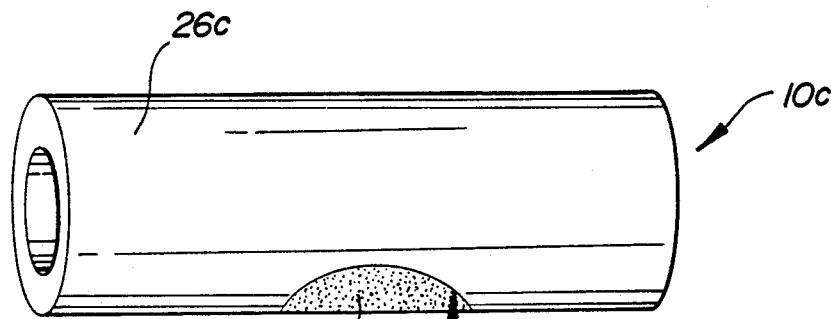
FIG. 5 is a perspective view of a third embodiment of the subject invention.

FIG. 5 illustrates the third embodiment of the assembly 10c wherein the hollow cylinder of the cushion pad 26c includes the minimum sized recess 28c. However, the recess design of the first embodiment 10a may be utilized. The recess 28c includes a filler element 36 of a second predetermined resiliency and hardness which is less than the first predetermined resiliency and hardness. The filler element 36 fills the recess 28c but provides no significant support or pressure on the median nerve 24. The surrounding cushion pad 26c maintains the support of the hand 12 on the tool 14, and the filler element 36 provides an asthetically pleasing assembly 10 while not allowing pressure on the median nerve 24 by the filler element 36. The filler element 36 may be directly molded into the cushion pad 26c, or secured therein by an adhesive.

Figure 6:
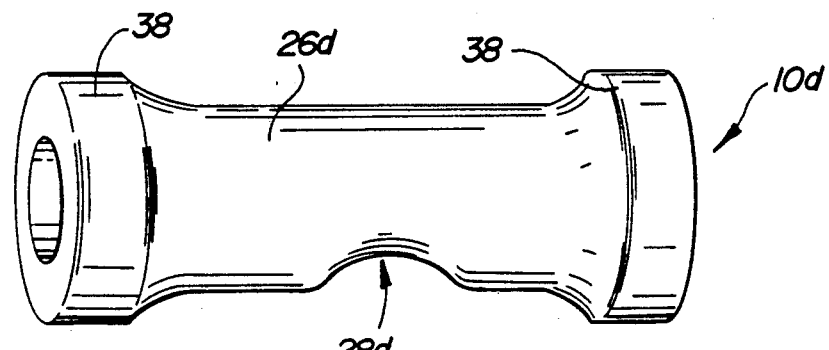
FIG. 6 is a perspective view of a fourth embodiment of the subject invention.

FIG. 6 illustrates the fourth embodiment of the assembly 10d which includes a cushion pad 26d having end flanges 38 radially extending from the ends of the cylindrical cushion pad 26d for positioning the median nerve 24 over the recess 28d. The end flanges 38 position the palm of the hand 12 so that the median nerve 24 is protected by the recess 28d. The recess 28d is of the minimum size and the end flanges 38 ensure that the hand 12 and median nerve 24 is properly positioned over the recess 28d.

Figure 7:
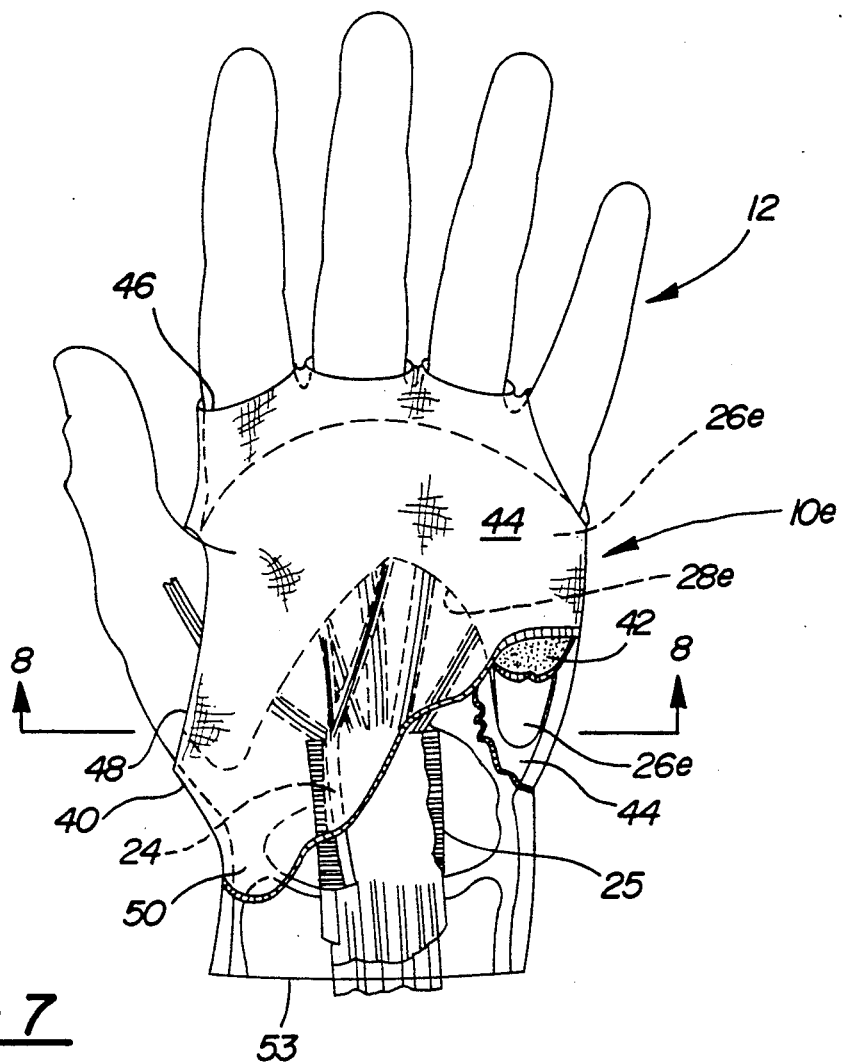
FIG. 7 is a partially cut-away view of a fifth embodiment of the subject invention.
Figure 8:
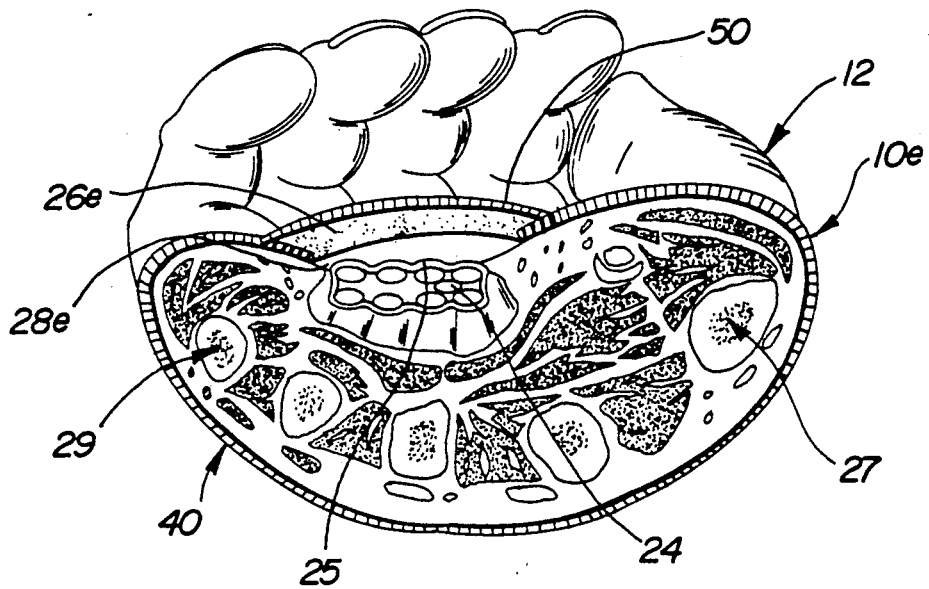
FIG. 8 is a partially cut-away view along lines 8—8 of FIG. 7.

The fifth embodiment of the assembly 10e utilizes a hand glove 40 to which is secured the cushion pad 26e as illustrated in FIGS. 7 and 8. The hand glove 40 includes finger holes 46 for receiving the fingers of the hand 12, a thumb hole 48 for receiving the thumb of the hand 12, a palm material 50 covering the palm of the hand 12, and a wrist band 53 for securing the hand glove 40 onto the hand 12. The cushion pad 26e is generally a flexible flat-shaped pad with the recess 28e therein. The cushion pad 26e is secured to the palm material 50 by either an adhesive 42, or is secured between two sheets of material 44 of the glove 40. The hand glove 40 is placed on the hand 12 of the user so that the cushion pad 26e is positioned against the hand 12 so that the median nerve 24 is over the recess 28e. The user may then grip any tool 14 while the cushion pad 26e prevents depression of the median nerve 24.

The embodiments of the cushion pad 26a-e described hereinabove may include any combination of features; i.e., the filler element 36, finger 32 and thumb 34 recesses, adhesive 30, etc.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A hand grip assembly for placement between a tool and a palm of a hand having a median nerve (24), said assembly comprising: support means (16) having first (18) and second (20) sides for receiving the gripping pressure of a palm of a hand (12) on said first side (18) and receiving a tool (14) on said second side (2), said support means (16) having a support axis for placement substantially perpendicular to the median nerve (24) when gripped by the palm of a hand; said first side of said support means (16) including protection means (22) recessed relative to the remainder of said first side (18) and extending perpendicular to said support axis and coaxial with the median nerve when gripped by the palm of the hand for eliminating the gripping pressure directly over the median nerve (24) of the hand (12) while the remainder of said first side (18) of said support means (16) supports the palm of the hand (12) at portions parallel with and adjacent to said protection means (22), said support means (16) including a cushion pad (26) of a first predetermined resiliency and hardness, said protection means (22) including a recess (28) within the cushionpad (26) and within a predetermined size range extending beyond the width of the median nerve for eliminating pressure directly over and in the vicinity of the median nerve (24), said protection means (22) including filler means (36) of a second predetermined resiliency and hardness less than said first predetermined resiliency and hardness for filling said recess (28) to protect the median nerve (24) while inhibiting continuous pressure over the median nerve (24).

2. An assembly as set forth in claim 1 further characterized by said cushion pad (26) formed as a hollow cylinder for receiving the tool (14).

3. An assembly as set forth in claim 2 further characterized by said recess (28) comprising a groove extending about the circumference of said hollow cylinder of said cushion pad (26).

4. An assembly as set forth in claim 2 further characterized by said cushion pad (26) including a plurality of finger flanges (32) and a thumb flange (34) for positioning the median nerve (24) over said recess (28).

5. An assembly as set forth in claim 2 further characterized by said cushion pad (26) including radially extending flanges (38) extending perpendicular from said first side (18) at the ends of said hollow cylinder for positioning the median nerve (24) over said recess (28).

6. An assembly as set forth in claim 1 further characterized by including positioning means (32, 34, 38) connected to said cushion pad (26) for positioning the hand (12) against said cushion pad (26) so that the median nerve (24) is over said recess (28).

7. An assembly as set forth in claim 6 further characterized by including positioning means (32, 34, 38) comprising flanges extending from said cushion pad (26) for positioning the hand (14) over said recess (28).

8. A hand grip assembly for placement between a tool and a palm of a hand having a median nerve (24), said assembly comprising: support means (16) having first (18) and second (20) sides for receiving the gripping pressure of a palm of a hand (12) on said first side (18) and receiving a tool (14) on said second side (2), said support means (16) having a support axis for placement substantially perpendicular to the median nerve (24) when gripped by the palm of a hand; said first side of said support means (16) including protection means (22) recessed relative tot he remainder of said first side (18) and extending perpendicular to said support axis and coaxial with the median nerve when gripped by the palm of the hand for eliminating the gripping pressure directly over the median nerve (24) of the hand (12) while the remainder of said first side (18) of said support means (16) supports the palm of the hand (12) at portions parallel with and adjacent to said protection means (22); further characterized by said support means (16) including a cushion pad (26) of a first predetermined resiliency and hardness, said protection means 922) including a recess (28) within the cushionpad (26) and within a predetermined size range extending beyond the width of the median nerve for eliminating pressure directly over and in the vicinity of the median nerve (24), said cushion pad (26) being adapted to be secured about a grip of a tool (14) and including means (30) for securing said cushion pad (26) about the grip of the tool (14) to secure said recess (28) in a position for receiving the median nerve (24).

9. An assembly as set forth in claim 8 further characterized by said cushion pad (26) adapted to be secured about a grip of a tool (14) having a generally cylindrical shape longitudinally parallel with said support axis and including a recess extending perpendicular to said support axis comprising said protection means (22), and said support portion on said first side (18) extending parallel with and along said recess to distribute pressure away from the median nerve (24) and onto adjacent soft tissue of the palm.

10. A hand grip assembly for placement between a tool and a palm of a hand having a median nerve (24), said assembly comprising: support means (16) having first (18) and second (20) sides for receiving the gripping pressure of a pal m of a hand (12) on said first side (18) and receiving a tool (14) on said second side (20), said support means (16) having a support axis for placement substantially perpendicular to the median nerve (24) when gripped by the palm of a hand; said first side of said support means (16) including protection means (22) recessed relative to the remainder of said first side (18) and extending perpendicular to said support axis and coaxial with the median nerve when gripped by the palm of the hand for eliminating the gripping pressure directly over the median nerve (24) of the hand (12) while the remainder of said first side (18) of said support means (16) supports the palm of the hand (12) at portions parallel with and adjacent to said protection means, (22) said support means (16) including a cushion pad (26) of a first predetermined resiliency and hardness, said protection means (22) including a recess (28) within the cushionpad (26) and within a predetermined size range extending beyond the width of the median nerve for eliminating pressure directly over and in the vicinity f the median nerve, (24) said support means comprising glove means (40) adapted to be placed over the hand (12) and being secured to said cushion pad (26) to position said recess (26) over the median nerve (24).

11. An assembly as set forth in claim 8 or 10 further characterized by said protection means including a recess (28) having a length parallel with said support axis to extend beyond the width of a flexor retinaculum of the hand and a width perpendicular to said support axis to protect a flexor retinaculum between the crease of a wrist of the hand and a first crease of the palm from the wrist, said width greater than said length.

12. An assembly as set forth in claim 11 further characterized by said remainder of said first side (18) establishing the said recess extending perpendicular to said support axis and parallel with the median nerve for continuously supporting a themar eminence (27) and hypothemar eminence (29) of the palm of the hand.

13. A hand grip assembly for placement between a tool and a hand, said assembly comprising: a cushion pad (26) having a first side (18) for receiving a hand (12) and a second side (20) for receiving a grip of a tool, said cushion pad (26) having a support axis for placement substantially perpendicular with the median nerve (24) when gripped by the palm of the hand; said first side (18) of said cushion pad (26) including a recess (28) therein within a predetermined size range for extending coaxially along the median nerve to eliminate gripping pressure directly over the median nerve (24) of the hand (12), said recess having a length parallel with said support axis for extending beyond the width of a flexor retinaculum of the hand and a width perpendicular to said support axis and coaxial with the median nerve for protecting the flexor retinaculum between a crease of the wrist and a first crease of the palm from the wrist, said width greater than said length, and including glove means (40) adapted to be placed over the hand (12) and secured to said cushion pad (26) to position said recess (26) over the median nerve (24).

14. An assembly as set forth in claim 13 further characterized by including positioning means (32, 34, 38) connected to said cushion pad (26) for positioning the hand (12) against said cushion pad (26) so that the median nerve (24) is over said recess (28).

15. An assembly as set forth in claim 14 further characterized by including positioning means (32, 34, 38) comprising flanges extending from said cushion pad (26) for positioning the hand (14) over said recess (28).

16. An assembly as set forth in claim 13 or 1 by said cushion pad (26) adapted to be secured about a grip of a tool (140 and including means (30) for securing said cushion pad (26) about the grip of the tool (14) to secure said recess (28) in a position for receiving the median nerve (24).

17. A hand grip assembly for placement between a tool and a palm of a hand having a median nerve (24), said assembly comprising: support means (16) having first (18) and second (20) sides for receiving the gripping pressure of a palm of a hand (12) on said first side (18) and receiving a tool (14) on said second side (2), said support means (16) having a support axis for placement substantially perpendicular to the median nerve (24) when gripped by the palm of a hand; said first side of said support means (16) including protection means (22) recessed relative tot he remainder of said first side (18) and extending perpendicular to said support axis and coaxial with the median nerve when gripped by the palm of the hand for eliminating the gripping pressure directly over the median nerve (24) of the hand (12) while the remainder of said first side (18) of said support means (16) supports the palm of the hand (12) at portions parallel with and adjacent to said protection means (22), said support means (16) including a cushion pad (26) of a first predetermined resiliency and hardness and glove means (40) adapted to be placed over the palm of the hand (12) and secured thereto, and including said cushion pad (26) including a recess extending perpendicular to said support axis with said cushion pad (26) adjacent and parallel with said recess for distributing pressure away from the median nerve (24) and onto adjacent soft tissue to the palm.

18. An assembly as set forth in claim 17 further characterized by said recess having a width coaxial with the median nerve and perpendicular to said support means, and a length parallel with said support axis, said width being greater than said length.

* * * * *